(12) United States Patent
Skory

(10) Patent No.: US 6,268,189 B1
(45) Date of Patent: Jul. 31, 2001

(54) FUNGAL LACTATE DEHYDROGENASE GENE AND CONSTRUCTS FOR THE EXPRESSION THEREOF

(75) Inventor: Christopher D. Skory, Washington, IL (US)

(73) Assignee: The United States of America as represented by the Secretary of Agriculture, Washington, DC (US)

(*) Notice: Subject to any disclaimer, the term of this patent is extended or adjusted under 35 U.S.C. 154(b) by 0 days.

(21) Appl. No.: 09/535,381

(22) Filed: Mar. 24, 2000

(51) Int. Cl.[7] ............... C12P 7/56; C12N 9/04; C12N 1/20; C12N 1/14; C12N 1/16; C07M 21/04

(52) U.S. Cl. ............ 435/139; 435/190; 435/252.3; 435/252.33; 435/254.11; 435/254.21; 536/23.2; 536/23.7

(58) Field of Search ............... 435/190, 252.3, 435/252.33, 254.11, 254.21, 320.1; 536/23.2, 23.7

(56) References Cited

U.S. PATENT DOCUMENTS 4,963,486   10/1990   Hang ................... 435/139

FOREIGN PATENT DOCUMENTS 9914335   3/1999   (WO).

OTHER PUBLICATIONS

Yu, Rochi–chui et al., "Purification and Characterization of NAD–dependent Lactate Dehydrogenase from *Irhizopus oryzae*", *Food Chemistry*, 41, 1991, pp. 219–225.

Skory, Christopher D., et al., "Production of L–lactic acid by *Rhizopus oryzae* under oxygen limiting condition", *Biotechnol. Lett.*, vol. 20, No. 2, Feb., 1998, pp. 191–194.

Adachi, Eri et al., "Modification of Metabolic Pathways of *Saccharomyces cerevisiae* by the Expression of Lactate Dehydrogenase and Deletion of Pyruvate Decarboxylase Genes for the Lactic Acid Fermentation at Law pH Value", *Journal of Fermentation and Bioengineering*, vol. 86, No. 3, 1998, pp. 284–289.

*Primary Examiner*—Elizabeth Slobodyansky
*Assistant Examiner*—Yong Pak
(74) *Attorney, Agent, or Firm*—M. Howard Silverstein; Curtis P. Ribando; John D. Fado

(57) ABSTRACT

A fungal Ldh protein and a gene have been isolated from *Rhizopus oryzae*. Host organisms transformed with expression vectors containing this gene produce optically pure, or enhanced levels of L-(+)-lactic acid not characteristic of the wild type organisms. These transformants will be useful for providing an increased supply of lactic acid for use in food and industrial applications.

29 Claims, 3 Drawing Sheets

FUNGAL LACTATE DEHYDROGENASE GENE AND CONSTRUCTS FOR THE EXPRESSION THEREOF

BACKGROUND OF THE INVENTION

1. Field of the Invention

This invention relates to the isolation of a fungal lactate dehydrogenase (Ldh) from *Rhizopus oryzae,* to the gene encoding the Ldh, to nucleic acid constructs containing the gene, and to the expression of the gene in host transformants for the purpose of lactic acid production.

Lactic acid is commonly used as a food additive for preservation, flavor, acidity and for the manufacture of the biodegradable plastic, polylactic acid (PLA). The global lactic acid market is estimated to be in excess of 100,000 tons per year and is expected to increase substantially in next few years as new PLA facilities become operational. Another demand that may grow substantially is the biodegradable solvent ethyl lactate. This ester is considered non-toxic and has many applications that include electronic manufacturing, paints and coatings, textiles, cleaners and degreasers, adhesives, printing, and de-inking. It has been estimated that lactate esters could potentially replace as much as 80% of the 3.8 million tons of solvents used each year in the U.S. However, fermentation efficiency must be improved to ensure the economic feasibility of these anticipated market expansions.

2. Description of the Prior Art

Fermentative methods for production of lactic acid are often preferred over chemical synthesis which results in a mixture of both D and L isomers. The products of microbiological fermentations are dependent on the organism used. They may yield a mixture of the two isomers or optically pure acid in a stereospecific form. The desired stereospecificity of the product depends on the intended use. However, L-(+)-lactic acid is the most desired form for the majority of applications.

Bacterial fermentations with Lactobacilli are common for industrial production of lactic acid, but these fermentations rarely yield optically pure product. Additionally, the fastidious nature of these bacteria requires that considerable amounts of supplemental nutrients be added to the growth medium, adding additional cost and making purification more difficult. Yeast are not capable of producing appreciable levels of lactic acid, although recombinant *Saccharomyces cerevisiae* strains have been described that contain the ldh gene from either Lactobacillus or bovine origins [Patent WO 99/14335 and Adachi et al. J. Ferment. Bioeng. 86:284–289(1998)]. While capable of producing up to 2–4% (w/v) lactic acid, these strains exhibit poor productivity and a significant portion of the glucose is converted to ethanol.

The filamentous fungus *Rhizopus oryzae* (syn. *R. arrhizus*) is also used for industrial production of lactic acid. It was in 1936 that *R. oryzae* was first described as being able to aerobically convert glucose, in a chemically defined medium, to large amounts of optically pure L-(+)-lactic acid. Research on lactic acid production by Rhizopus has continued primarily because of the ease of product purification in a minimal growth medium and the ability of the fungus to utilize both complex carbohydrates and pentose sugars (Hang et al., U.S. Pat. No. 4,963,486). This allows the fungus to be utilized for conversion of low value agricultural biomass to lactic acid.

It is extraordinary to find a filamentous fungus, like *R. oryzae,* that converts such a high percentage of the available carbon source to a fermentative by-product such as lactic acid. Most eukaryotic organisms rely primarily on oxidative phosphorylation when oxygen is available and use fermentation as a means for regenerating $NAD^+$ only when necessary. Fermentation is much less energy efficient than oxidative phosphorylation, but is often necessary in the absence of oxygen to ensure the availability $NAD^+$ for continued glycolysis and ATP production. However, it has been suggested that there might be a selective advantage for an organism to convert available sugars to another compound that can still be utilized as an energy source. This is especially true if the fermentation by-product is not as desirable for other organisms that might be competing for the same starting sugars. Rhizopus is very acid tolerant, while most bacteria are inhibited by lactic acid. It may be less efficient for the fungus to ferment sugars to lactic acid, but it is a way to minimize competition by other microorganisms. Similar, theories have also been proposed for ethanologenic yeast that ferment most of the available sugar to ethanol instead relying primarily on oxidative phosphorylation.

Other metabolic products made by Rhizopus include, ethanol, fumaric acid, and glycerol. Production levels for the different metabolites vary tremendously among the Rhizopus species, with some producing predominantly lactic acid and others accumulating only fumaric acid. An ideal lactic acid producing strain of Rhizopus would accumulate little or none of these metabolites, since their production depletes sugar that could be used for conversion to lactate.

Ethanol is believed to be produced by most Rhizopus species primarily as a result of low oxygen conditions. While Rhizopus is not typically considered an organism that grows under anaerobic conditions, it does possess ethanol fermentative enzymes that allow the fungus to grow for short periods in the absence of $O_2$. These enzymes have not been purified to homogeneity, but the alcohol dehydrogenase proteins have been partially characterized.

Fumaric acid production has been well-studied in Rhizopus (U.S. Pat. No. 4,877,731) and the fumarase gene has also been isolated. Synthesis is believed to occur primarily through the conversion of pyruvate to oxaloacetate, by pyruvate dehydrogenase. Conditions leading to increased fumaric acid are usually associated with aerobic growth in high glucose levels and low available nitrogen. Accumulation of fumarate is often a problem with lactic acid production, because its low solubility can lead to detrimental precipitations that compromise the fermentation efficiency.

Glycerol is a byproduct that is often produced by Rhizopus grown in high glucose containing medium. There has not been much written specifically about this metabolite accumulation in Rhizopus, but it is likely that regulation is similar to that found in Saccharomyces. There are at least two genes that encode glycerol-3-phosphate dehydrogenase (EC 1.1.1.8) in these organisms. It appears that one of these genes is expressed primarily during anoxic conditions, so that glycerol may act as a redox sink for excess cytosolic NADH. The other gene is involved in osmoregulation and is turned on during osmotic stress. Accumulation of the glycerol is presumably to allow the cell to maintain turgor pressure in the presence of high sugars or salts. Mutants deleted for both activities do not produce detectable glycerol, are highly osmosensitive, and are unable to grow under reduced oxygen conditions.

The ability to modify lactic acid production by genetic modification in Rhizopus and other fungi has been limited. Efforts in this area have been hampered by the lack of cloned ldh genes, encoding functional $NAD^+$ dependent L-lactate dehydrogenase, of fungal origin. Such a gene would have distinct advantages for expression in filamentous fungi and yeast.

SUMMARY OF THE INVENTION

I have now, for the first time, isolated a fungal Ldh protein and a gene encoding that protein. I have also constructed expression vectors with these genes, transformed host organisms with the vectors, and observed enhanced levels of optically pure L-(+)-lactic acid when the transformants were cultivated on a fermentable medium.

In accordance with this discovery, it is an object of this invention to provide a novel Ldh protein and ldh gene for use in lactic acid production.

It is another object of this invention to make constructs for use in transforming any of numerous host organisms for expressing the ldh gene when the host organism is cultivated in a fermentable medium.

It is also an object of the invention to enhance the L-(+)-lactic acid production of lactic acid-producing organisms and to introduce L-(+)-lactic expression in non-lactic acid-producing organisms.

A further object of the invention is to provide an increased supply of lactic acid for use in food and industrial applications.

Other objects and advantages of this invention will become readily apparent from the ensuing description.

DEPOSIT OF BIOLOGICAL MATERIAL

Figure 1:
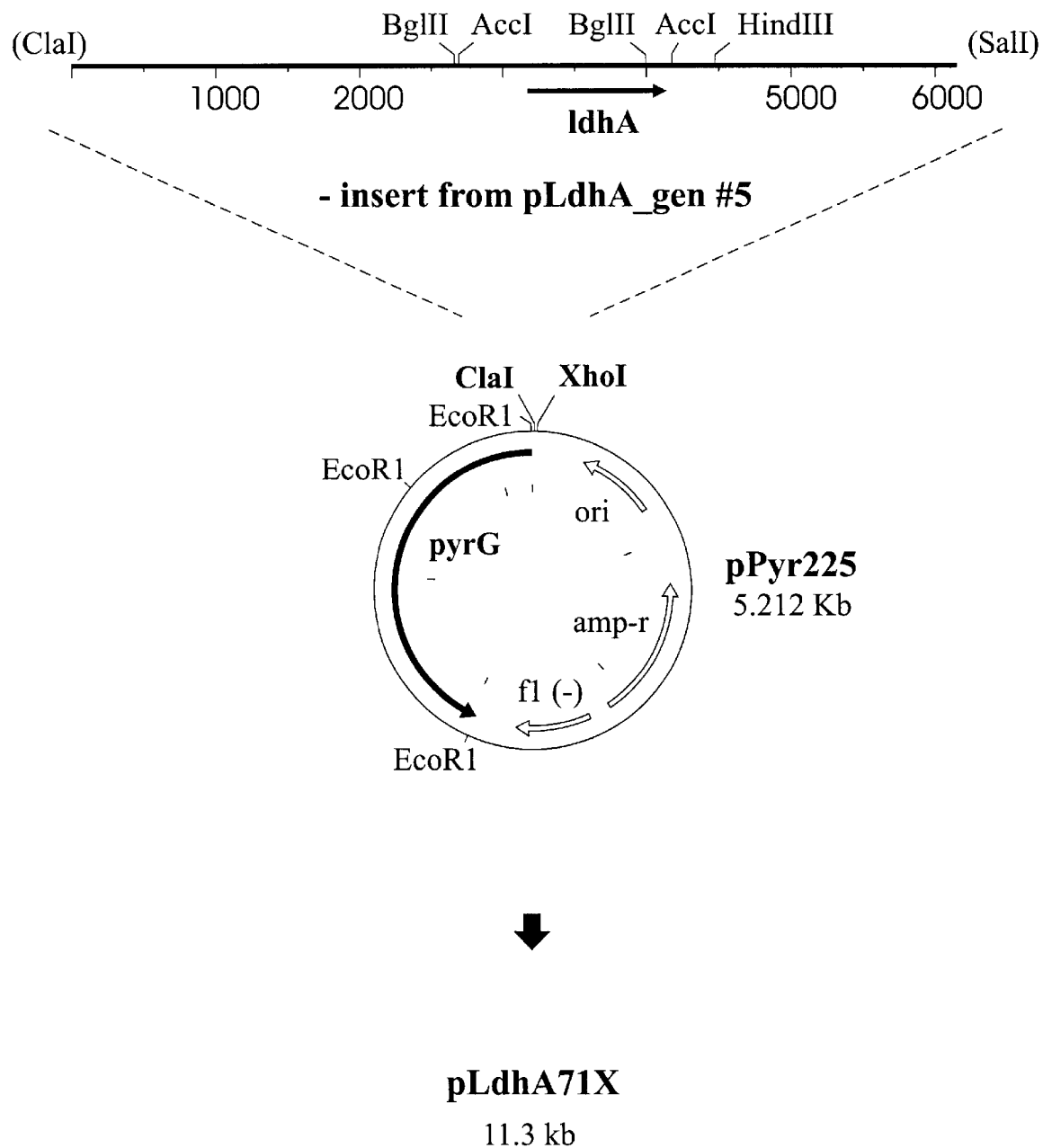
FIG. 1 is a map of a transformation shuttle plasmid, pPyr225 comprising a 2.25 kb pyrG containing fragment isolated from *R. oryzae* NRRL 395. Ligation of a 6.1 kb fragment containing the *R. oryzae* ldha gene to ClaI/XhoI linearized pPyr225 resulted in plasmid pLdhA71X.

Purified cultures of a *Rhizopus oryzae* Pyr-17 (pLdhA71X), *Escherichia coli* DC1368 (pLdhA74IX), and *Saccharomyces cerevisiae* DAY4 (pLdhA68X) were deposited on Mar. 14, 2000, in the U.S. Department of Agriculture, Agricultural Research Service Culture Collection in Peoria, Ill., under the terms of the Budapest Treaty, and have been assigned Accession Numbers NRRL 30272, NRRL B-30273, and NRRL Y-30271, respectively.

DEFINITIONS

The following terms are employed herein:

Cloning. The selection and propagation of (a) genetic material from a single individual, (b) a vector containing one gene or gene fragment, or (c) a single organism containing one such gene or gene fragment.

Cloning Vector. A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transformed cells, e.g., uracil utilization, tetracycline resistance, ampicillin resistance. A cloning vector may or may not possess the features necessary for it to operate as an expression vector.

Codon. A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

Complement or Complementary Sequence. The product of complementary base pairing in which purines bond with pyrimidines, as occurs in the two polynucleotide chains of DNA (adenine with thymine, guanine with cytosine) and between DNA and messenger RNA nucleotides during transcription.

DNA Coding Sequence. A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eucaryotic mRNA. A polyadenylation signal and transcription termination sequence will usually be located 3' to the coding sequence.

DNA Sequence. A linear series of nucleotides connected one to the other by phosphodiester bonds between the 3' and 5' carbons of adjacent pentoses.

Expression. The process undergone by a structural gene to produce a polypeptide. Expression requires both transcription of DNA and translation of RNA.

Expression Vector. A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fumaric Acid. The term "fumaric acid" in this application refers to total trans-1,2-ethylenedicarboxylic acid in either the free acid or salt form. The salt form of fumaric acid is referred to as "fumarate" regardless of the of the neutralizing agent, i.e., calcium carbonate or ammonium hydroxide.

Fusion Protein. A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene. A segment of DNA which encodes a specific protein or polypeptide, or RNA.

Genome. The entire DNA of an organism. It includes, among other things, the structural genes encoding for the polypeptides of the substance, as well as operator, promoter and ribosome binding and interaction sequences.

Heterologous DNA. A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization. The pairing together or annealing of single stranded regions of nucleic acids to form double-stranded molecules.

Lactic Acid. The term "lactic acid" in this application refers to total 2-hydroxypropionic acid in either the free acid or salt form. The salt form of lactic acid is referred to as "lactate" regardless of the of the neutralizing agent, i.e., calcium carbonate or ammonium hydroxide.

Nucleotide. A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage. Bacterial virus many of which include DNA sequences encapsidated in a protein envelope or coat ("capsid"). In a unicellular organism, a phage may be introduced by a process called transfection.

Plasmid. A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. A cell transformed by a plasmid is called a "transformant".

Polypeptide. A linear series of amino acids connected one to the other by peptide bends between the alpha-amino and carboxy groups of adjacent amino acids.

Promoter. A DNA sequence within a larger DNA sequence defining a site to which RNA polymerase may bind and initiate transcription.

Reading Frame. The grouping of codons during translation of mRNA into amino acid sequences. During translation the proper reading frame must be maintained. For example, the DNA sequence may be translated via mRNA into three reading frames, each of which affords a different amino acid sequence.

Recombinant DNA Molecule. A hybrid DNA sequence comprising at least two DNA sequences, the first sequence not normally being found together in nature with the second.

Ribosomal Binding Site. A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Start Codon. Also called the initiation codon, is the first mRNA triplet to be translated during protein or peptide synthesis and immediately precedes the structural gene being translated. The start codon is usually AUG, but may sometimes also be GUG.

Structural Gene. A DNA sequence which encodes through its template or messenger RNA (mRNA) a sequence of amino acids characteristic of a specific polypeptide.

Substantially Pure. The condition of a compound, such as a protein or a nucleotide, being cell free or being separated from other components that would interfere with or have a substantial qualitative effect on the activity of the compound or on a substrate on which the compound acts.

Transform. To change in a heritable manner the characteristics of a host cell in response to DNA foreign to that cell. An exogenous DNA has been introduced inside the cell wall or protoplast. Exogenous DNA may or may not be integrated (covalently linked) to chromosomal DNA making up the genome of the cell. In procaryotes and some fungi, for example, the exogenous DNA may be maintained on an episomal element such as a plasmid. With respect to most eucaryotic cells, a stably transformed cell is one in which the exogenous DNA has been integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription. The process of producing mRNA from a structural gene.

Translation. The process of producing a polypeptide from mRNA.

DETAILED DESCRIPTION

The novel fungal ldh gene of the invention is believed to be uniquely functional in regard to enhancing the production of lactic acid when expressed in a host system. Of particular interest is ldhA isolated from *Rhizopus oryzae*. The sequence of the *R. oryzae* ldhA gene is given below in *R. oryzae* SEQ ID NO 1 and has been deposited in GenBank (Accession #AF226154, Jan. 14, 2000). It is part of a larger 6.1 kb fragment (SEQ ID NO 3), originally isolated from *R. oryzae* NRRL 395 and includes not only the ldhA gene, but also regions of primarily untranslated DNA.

Because of the degeneracy of the genetic code, there exists a finite set of nucleotide sequences which can code for a given amino acid sequence. It is understood that all such equivalent sequences are operable variants of the disclosed sequence, since all give rise to the same protein (i.e., the same amino acid sequence) during in vivo transcription and translation, and are hence encompassed by the instant invention. Of particular interest herein are those nucleotide sequences that encode for the Ldh enzyme having the amino acid sequence represented by SEQ ID NO 2.

Two polynucleotides or polypeptides are said to be "identical" if the sequence of nucleotides or amino acid residues, respectively, in the two sequences is the same when aligned for maximum correspondence as described below.

Sequence comparisons between two (or more) polynucleotides or polypeptides are typically performed by comparing sequences of the two sequences over a segment or "comparison window" to identify and compare local regions of sequence similarity. Optimal alignment of sequences for comparison may be conducted by the local homology algorithm of Smith and Waterman [*Adv. Appl. Math.* 2:482 (1981)], by the homology alignment algorithm of Needleman and Wunsch [*J. Mol. Biol.* 48:443 (1970)], by the search for similarity method of Pearson and Lipman [*Proc. Natl. Acad. Sci. (U.S.A)* 85:2444 (1988)], by computerized implementations of these algorithms [(GAP, BESTFIT, FASTA, and TFASTA in the Wisconsin Genetics Software Package, Genetics Computer Group (GCG), 575 Science Dr., Madison, Wis.], or by inspection. "Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences as used herein means that a polynucleotide comprises a sequence that has at least 60% sequence identity, preferably at least 80%, more preferably at least 90% and most preferably at least 95%, compared to a reference sequence using the programs described above using standard parameters. The reference sequence herein is either the ldhA coding region defined by SEQ ID NO 1 or a region of SEQ ID NO 3 comprising the ldhA coding and regulatory regions. One of skill in the art will recognize that the aforementioned percentage values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 50%, preferably at least 60%, more preferably at least 90%, and most preferably at least 95% compared to a reference sequence. The reference sequence herein is the ldhA translation product (amino acid sequence) defined by SEQ ID NO 2. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other under stringent conditions. Stringent conditions are sequence dependent and will be different in different circumstances. Generally, stringent conditions are selected to be about 5° C. to about 20° C. lower than the thermal melting point (Tm) for the specific sequence at a defined ionic strength and pH. The Tm is the temperature (under defined ionic strength and pH) at which 50% of the target sequence hybridizes to a perfectly matched probe. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code.

Of course, it is understood that the invention is intended to cover only those nucleotide sequences that encode, and only those amino acid sequences that represent, a functional Ldh enzyme useful for reducing pyruvate to lactate as herein described.

The DNA sequences of the invention can be used to prepare recombinant DNA molecules by cloning into any suitable vector. A variety of vector-host cell expression systems may be employed in practicing the present invention. Strains of bacteria, such as *Escherichia coli,* and strains of yeast (for example, *Saccharomyces cerevisiae*) and other fungi, such as *R. oryzae,* are particularly useful in producing lactic acid in the practice of the invention. However, the novel invention described here can be applied with numerous hosts that would desirable for various lactic acid producing schemes. Host strains may be of bacterial, fungal, or yeast origin. Factors that can be considered in choosing host strains include substrate range, hardiness, sugar tolerance, salt tolerance, temperature tolerance, pH tolerance, and lactate tolerance. Ascertaining the most appropriate host-vector system is within the skill of the person in the art.

Vectors used in practicing the present invention are selected to be operable as cloning vectors or expression vectors in the selected host cell. Numerous vectors are known to practitioners skilled in the art, and selection of an appropriate vector and host cell is a matter of choice. The vectors may, for example, be bacteriophage, plasmids, viruses, or hybrids thereof, such as those described in Maniatis et al. [Molecular Cloning: A Laboratory Manual, Cold Springs Harbor Laboratory, 1989 or Ausubel et al., Current Protocols in Molecular Biology, John Wiley & Sons, Inc, 1995], herein incorporated by reference. Further, the vectors may be non-fusion vectors (i.e., those producing the LdhA protein of the invention not fused to any heterologous polypeptide), or alternatively, fusion vectors (i.e., those producing the LdhA protein fused to a vector encoded polypeptide). The fusion proteins would of course vary with the particular vector chosen.

Within each specific vector, various sites may be selected for insertion of the isolated DNA sequence. These sites are usually designated by the restriction enzyme or endonuclease that cuts them.

The particular site chosen for insertion of the selected DNA fragment into the vector to form a recombinant vector is determined by a variety of factors. These include size and structure of the polypeptide to be expressed, susceptibility of the desired polypeptide to enzymatic degradation by the host cell components and contamination by its proteins, expression characteristics such as the location of start and stop codons, and other factors recognized by those of skill in the art. None of these factors alone absolutely controls the choice of insertion site for a particular polypeptide. Rather, the site chosen reflects a balance of these factors, and not all sites may be equally effective for a given protein.

The DNA sequences comprising the ldh gene of the invention may be inserted into the desired vector by known techniques. If, however, the vector is to serve as an expression vector, the vector should have a promoter, and the DNA sequence should be inserted in the vector downstream of the promoter and operationally associated therewith (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence of the invention once inserted (in correct translational reading frame therewith). The vector should be selected to provide a region which codes for a ribosomal binding site recognized by the ribosomes of the host cell into which the vector is to be inserted. The vector should contain a terminator with necessary 3' untranslated sequences for RNA termination, stability, and/or poly (A) tail addition (if eucaryotic). Alternatively, any or all of the above control sequences may be ligated to the coding sequence prior to insertion into the vector.

DNA constructs may be introduced into the appropriate host by numerous methods described in the technical and scientific literature. Transformation of bacteria or yeast may be performed using standard techniques described in Maniatis et al., supra. Techniques for transforming filamentous fungi may include those described by Goosen et al. [*Handbook for Applied Mycology*, pp. 151–195 (Arora, Elander, and Mukerji, eds. (1992)] and May et al. [*Applied Molecular Genetics of Filamentous Fungi*, pp. 1–27 (Kinghorn and Turner, eds. (1992)]. Transformations with Rhizopus are described in Example 1.

In general, linear or circular DNA constructs may be introduced into the host fungus by techniques utilizing protoplast fusion, polyethylene glycol, liposomes, lithium acetate, electroporation, physical damage, biolistic bombardment, or Agrobacterium mediated transformation.

Successful transformants may be isolated by using markers, contained on the expression vectors, which confer a selectable trait to the transformed host. These may include nutritional selection related to substrate utilization (such as, growth on acetamide containing medium) or prototrophy of a required growth product (such as, arginine, leucine, or uracil). Dominant selectable markers (such as, resistance to G418, hygromycin, and phleomycin) are also useful in selecting transformants that have taken up the introduced DNA construct.

The DNA construct may be replicated autonomously or integrated into the genome of the host. Integration typically occurs by homologous recombination (for example, arginine selectable marker integrating in the chromosomal arginine gene) or at a chromosomal site unrelated to any genes on the DNA construct. Integration may occur by either a single or double cross-over event. It is also possible to have any number of these integration and replication types occurring in the same transformant.

In selecting fungal transformants in accordance with the invention, the utilization of uracil is a useful selective marker. There are two enzymatic steps required for the conversion of orotic acid to uridine monophosphate. One step utilizes OMP pyrophosphate (encoded by the pyrF gene) and the other utilizes OMP decarboxylase (encoded by the pyrG gene). In the Examples below, it was decided to use auxotrophs that were deficient in OMP-decarboxylase activity, encoded by pyrG, but which still bore a functional pyrF gene. Depending on the desired application, the DNA construct may be replicated autonomously or integrated into the host genome.

Production of the Ldh protein by successfully transformed hosts may be constitutive or regulated to produce the protein only under certain conditions. This type of regulation is most easily controlled at the transcriptional level. An example would include a promoter which can be regulated by adjusting conditions in the environment, such that the cells can be grown under conditions where expression of the ldh gene is minimal or absent. Production of the protein may be induced by appropriate manipulation of conditions. This protocol may be used to prevent premature accumulation of the protein which may be harmful to the growth of the cell. The promoter for the *R. oryzae* ldh gene can be regulated by the presence or absence of a fermentable carbon source as described in Example 7. While this regulation is not utilized as such in the present invention, it is understood that it is encompassed by the invention.

The recombinant Ldh enzyme is produced intra-cellularly and functions to catalyze the conversion of pyruvate to lactate. The resultant lactate is then secreted by the cell into the medium wherein it can be recovered from the medium using suitable techniques generally known in the art.

It is presumed that the host organism will already have functional metabolic pathways for the utilization of pyruvate. For many bacteria and fungi, pyruvate is a major branch point for fermentative (reduction) or respiratory (oxidative) pathways. The recombinant enzyme must therefore compete for available pyruvate that might otherwise be utilized in these pathways. Metabolites accumulated as a result of these pathways are considered byproducts and decrease the efficiency of lactate production.

Fermentation parameters are dependent on the type of regulatory mechanisms used to control ldh expression for the DNA construct and the host organism used for production of the recombinant enzyme. Conditions must be such that ldh genes are expressed at levels that facilitate the production and accumulation of lactic acid by the recombinant host, as a result of the DNA construct. Growth medium may be minimal/defined (such as, similar to Rhizopus fermentations in Example 4) or complete/complex (such as, similar to fermentation in Examples 5 and 6). Fermentable carbon source could include hexose and pentose sugars, starch, cellulose, xylan, oligosaccharides, and combinations thereof.

Growth and production of the lactate can be performed in normal batch fermentations, fed-batch fermentations or continuous fermentations. It may be desirable to perform fermentations under reduced oxygen or anaerobic conditions for certain hosts. Lactate production with Rhizopus will require some oxygen and the use of air-lift or equivalent fermentors are often preferred. Temperature of the fermentation should be at least 25° C.

The pH of the fermentation should be sufficiently high enough to allow growth and lactate production by the host. Adjusting the pH of the fermentation broth may be performed using neutralizing agents such as calcium carbonate or hydroxides. Alternatively, lactic acid can be removed continuously during the fermentation using methods such as membrane technology, electro-dialysis, solvent extraction, and absorbent resins. The selection and incorporation of any of the above fermentative methods is highly dependent on the host strain and the preferred downstream process.

The following examples are intended to further illustrate the invention, without any intent for the invention to be limited to the specific embodiments described therein.

EXAMPLE 1

Development of Transformation Methods for *R. oryzae*

A. Isolation and Analysis of *R. oryzae* NRRL 395 Uracil Mutants

Germinating sporangiospores were mutated with nitrosoguanidine by the methods of Skory et al. [Biotech. Letts. 20:191–194 (1998)] and then distributed to eighteen potato dextrose agar (PDA) plates containing 0.5 mg uracil/ml. Plates were incubated to allow growth and sporulation under non-selective conditions in order to segregate mutant alleles. Sporangiospores from each plate were transferred to Difco® yeast nitrogen base (YNB) supplemented with 2.5 mg 5-fluorootic acid (FOA)/ml and 0.5 mg uracil/ml. FOA is toxic to uracil prototrophic cells, due to the formation of the nucleotide analogue 5-fluorouracil.

FOA resistant colonies were obtained from each of the eighteen selective plates. One colony from each of the plates was transferred to a new plate to confirm resistance to FOA and all except one were able to continue growth under selective conditions. Transfer of spores onto minimal medium with and without uracil revealed that all seventeen of the isolates were uracil auxotrophs.

Two enzymatic steps are required for the conversion of orotic acid to uridine monophosphate. Isolates deficient in OMP pyrophosphorylase (encoded by the pyrF gene) were differentiated from those deficient in orotidine monophosphate (OMP) decarboxylase (encoded by the pyrG gene) by $^{14}C$ analysis.

Enzymatic analyses were similar to that described by Skory et al. [*Appl. Environ. Microbiol.* 56:3315–3320 (1990)] where cell-free protein extracts from each of the FOA-resistant mutants were incubated with either $^{14}C$-orotic acid (plus 5-phoribosyl pyrophosphate) or $^{14}C$-OMP. Reactions were stopped and proteins precipitated by cold methanol. An aliquot of the supernate was then separated by TLC using polyethyleneimine-cellulose plates, with 0.75M TrisCl (pH 8) as solvent. TLC plates were dried and exposed to Kodak XAR film for 5 days at −80° C.

Enzymatic analyses showed that five of the seventeen uracil auxotrophs were deficient in OMP-decarboxylase activity, encoded by pyrG, while still having a functional OMP-pyrophosphorylase. *R. oryzae* NRRL 395 served as a control to demonstrate the ability to complete both conversion steps. One of the pyrG mutants, Pyr-17, was chosen for transformation after determining that it had a reversion frequency of $<10^9$. No detectable germination or spore swelling, with this mutant, occurred on minimal medium lacking uracil.

B. Isolation of the *Rhizopus oryzae* OMP-decarboxylase Gene

Genes coding for the OMP-decarboxylase proteins from *Rhizopus niveus, Mucor circinelloides,* and *Phycomyces blakesleeanus* were compared to find conserved regions. These locations were then used to develop degenerate oligonucleotide primers for polymerase chain reaction of genomic DNA. DNA fragments obtained using PCR with degenerate primers were shown to have sequences similar to other pyrG (or equivalent) genes. The largest of the fragments, 544 bp, was amplified with the primers defined by IUB code [Eur. J. Biochem. 150:1–5 (1985)] as having the sequences 5'- ATT GAY ATT GTK GAA GAC TTY GA (SEQ ID NO 4) and 5'- CCA CTC TCM ACA ATN ACT TC (SEQ ID NO 5). This fragment was purified and used as a probe to obtain the *R. oryzae* NRRL 395 pyrG gene from a genomic DNA library prepared with Lambda Zap Express® (Stratagene®, La Jolla, Calif.) according to the manufacture's protocol.

Several overlapping fragments were isolated from the genomic library. The location of the pyrG gene was determined by subcloning and sequencing of the genomic isolate. The presence of introns were determined by sequencing internal regions of the gene obtained by PCR amplification using cDNA as template. The coding region was 98% identical to the *R. niveus* pyr4 gene, while the percent identity of the flanking promoter and terminator regions was closer to 90% [Horiuchi et al. Curr. Genet. 27:472–478 (1995); U.S. Pat. No. 5,436,158]. The locations of start/stop codons were inferred from sequence comparisons with other pyr genes.

C. Introduction of Transformation Vector into Host

A partially digested 2.25 Kb EcoR1 fragment (FIG. 1), containing the pyrG in its entirety, was subcloned into the EcoR1 site in pBluescript II KS- (Stratagene®). This vector was designated pPyr225 and served as the transformation shuttle plasmid.

Transformation of *R. oryzae* pyrG mutant Pyr-17 was performed using microprojectile particle bombardment (BioRad, Hercules, Calif.). Optimal conditions for transformation included using tungsten (M5) particles for DNA delivery and 1,100 psi rupture discs. Distance between the rupture disk and tungsten particle carrier was minimized to the greatest allowable force (approx. 1 cm) and the distance between the launch assembly and the target was 8 cm. Plasmid DNA was coated onto the tungsten particles according to manufacture's recommendations. Ungerminated spores were transformed directly on minimal medium plates, since no recovery time on non-selective medium was required.

Biolistic transformation with circular plasmids consistently yielded numerous prototrophic colonies that appeared within 3–4 days. The rate of growth for transformants transferred to new minimal medium was comparable to that of the original *R. oryzae* NRRL 395 parent strain. However, stability of the prototrophic phenotype was unstable with multiple transfers on non-selective medium. Southern analysis confirmed that plasmids were replicating autonomously with multiple copies of the recombinant plasmid per nuclei. Rearrangements of the plasmid could not be detected and are assumed to be a rare event.

EXAMPLE 2

Isolation of ldhA Gene

A. Preparation of Genomic and cDNA Libraries

*R. oryzae* NRRL 395 DNA was purified by CTAB extraction, partially digested by Sau3A, and used for the construction of a genomic library in Lambda Zap Express® (Stratagene®, La Jolla, Calif.) according to the manufacturer's recommendations. For the cDNA library, *R. oryzae* spores were first germinated for 24 hr with shaking at 30° C. in RZ medium supplemented with 10% (w/v) glucose. Calcium carbonate chips (Malinckrodt Baker, Paris, Ky.) were added to control pH and the incubation was continued for an additional 8 hrs before harvesting the mycelium for isolation of RNA by a hot phenol method. The cDNA library was prepared according to the manufacturer's recommendations for the Lambda Zap® unidirectional cDNA Synthesis Kit (Stratagene®).

RZ-medium (per liter)

$NH_4SO_4$ 2.0 g $KH_2PO_4$ 0.5 g $K_2HPO_4$ 0.2 g $MgSO_4$ 0.25 g $ZnSO_4$ 0.089 g

B. Isolation of ldh Genes

A method of anchored PCR with a degenerate primer was used to isolate a ldh gene fragment from *R. oryzae*. The degenerate primer as defined by IUB code as having the sequence 5'- SWR TCD CCR TGY TCA CC -3' (SEQ ID NO 6) was designed to preferentially anneal to a region encoding consensus amino acid motif GEHGDS involved in substrate binding and proton transfer for NAD$^+$ dependent L-lactate dehydrogenases. This primer was used with M13-reverse to amplify the upstream region of ldh from the cDNA library. A 600 bp fragment was recovered and TA-cloned into pCRII/TOPO (Invitrogen, Carlsbad, Calif.). Sequence analysis confirmed that the fragment represented a partial ldh gene. A probe was made from the gel-purified fragment and used to isolate hybridizing clones from both genomic and cDNA libraries.

Two genes, ldhA and ldhB, encoding NAD$^+$ dependent L-lactate dehydrogenase were cloned and sequenced. The genes are very similar to each other with greater than 90% nucleotide sequence identity and contain no introns. These clones are the first ldh genes from a fungus and sequence comparisons reveal that they are distinct from previously isolated prokaryotic and eukaryotic ldh genes. The deduced protein sequences are only 34–42% similar to other NAD$^+$ dependent Ldh subunits, as calculated by pairwise Lipman-Pearson comparisons.

R. oryzae NRRL 395 was grown on RZ medium as described in Example 2. Protein was precipitated from homogenized cells and ultimately purified by denaturing PAGE. Protein corresponding to the predominant semi-pure 36 kDa Ldh enzyme was eluted, digested, and sequenced by the Protein/DNA Technology Center of the Rockefeller University.

Protein sequencing of at least 69 amino acids of Ldh isolated from R. oryzae during lactic acid production confirmed that ldhA codes for a 36 KDa protein that converts pyruvate to lactate. Production of LdhA was greatest with sugars capable of being fermented to lactic acid, while ldhB transcripts could only be detected when R. oryzae was grown with non-fermentable carbon sources such as, glycerol, ethanol, and lactate. The product of ldhB is unknown.

EXAMPLE 3

Transformation of ldhA into R. oryzae Pyr-17

A. Transformation

The selection system described in Example 1 was used to introduce additional copies of the ldhA gene isolated in Example 2 into R. oryzae Pyr-17. Plasmid pPyr225 served as the selectable vector and a ldha-containing fragment was obtained from plasmid pLdhA_gen #5, that was isolated from a genomic DNA library. Restriction endonuclease digestion of this plasmid with SalI/ClaI released the 6.1 kb ldhA insert from the phagemid vector pBK-CMV (Stratagene®, LaJolla, Calif.). The gel-purified fragment was then ligated to plasmid pPyr225 which had been linearized with XhoI/ClaI. This ligation is possible because XhoI and SalI have compatible restriction overhangs. The resulting plasmid was called pLdhA71X. A large ldha-containing fragment was chosen to ensure that promoter and/or regulatory regions were represented.

Plasmid pLdhA71X was transformed into R. oryzae Pyr-17 using biolistic transformation, as described above. Selection of transformants was performed on RZ agar medium supplemented with 0.5% (w/v) glucose, RZ-glu. Spores were isolated and combined from all of the transformant clones and stored at −80° C. in 15% (v/v) glycerol. Aliquots of these spores were inoculated onto RZ-glu or RZ medium with 0.5% (w/v) glycerol and 0.5% (w/v) Difco® casamino acids, RZ-gly/caa. Growth and sporulation was more vigorous on the RZ-gly/caa medium. Spores were collected from the new medium and absorbed onto silica gel according to common microbiological techniques for long term storage of fungal spores. This silica gel stock serves as a reproducible inoculum for further analysis of the transformant clones, herein referred to as "R. oryzae Pyr-17 (pLdhA71X)".

B. Transcription and Enzyme Analysis of R. oryzae Pyr-17 (pLdhA71X) Transformant Silica stocks were used to inoculate RZ-gly/caa plates with R. oryzae Pyr-17 (pLdhA71X) transformant and wild-type R. oryzae NRRL 395. Spores obtained from each of these cultures were inoculated equally into three separate flasks containing 20 ml RZ supplemented with 1.5% glycerol and 0.5% trypticase peptone. Reductive Ldh activity from the ldhA gene is not detected in R. oryzae grown in this medium. Cultures were incubated for 16 hrs at 30° C. and with shaking at 200 rpm. An equal volume of RZ supplemented with 4% glucose was added for a final glucose concentration of 2%. Incubation continued as before for 5.5 hrs to allow for both transcriptional and translational induction of the ldhA. Mycelium was then quickly harvested and used for analysis by Southern and northern hybridization techniques and enzymatic detection of Ldh as described below.

Southern analysis of total genomic DNA digested with HindIII showed that plasmid pLdhA71X was replicating autonomously in the transformant clones (data not shown). Relative intensities of the plasmid and genomic ldhA gene indicated that there were at least 2–3 copies of recombinant plasmid for each copy of the genomic ldhA. RNA isolated from these cultures were used for northern analysis to show that ldha transcript is also present 2–3 fold higher in the recombinant strain when compared to the control (data not shown).

Enzymatic studies further established that additional copies of ldhA in the transformant clones, resulted in higher levels of reductive lactate dehydrogenase activity (Table I). The average specific activity for R. oryzae Pyr-17 (pLdhA71X) was 62% higher than the control. Reductive Ldh activity (pyruvate to lactate) was assayed spectrophotometrically by measuring the first order change in absorbance at 340 nm as a result of the oxidation of NADH. Reactions were performed with 175 $\mu$M NADH in 0.1 M bis-tris-propane, pH 6.8 and initiated with the addition of sodium pyruvate to a final concentration of 4 mM. All protein concentrations were adjusted to ensure that the change in absorbance followed first order kinetics for a minimum of 3–5 minutes. Assays were all performed in triplicate and one unit of enzyme activity is defined as the amount activity necessary to convert 1 $\mu$mole NADH to NAD$^+$. Protein concentrations were determined using the Biorad® Protein Assay kit.

EXAMPLE 4

Fermentation Studies with R. oryzae (pLdhA71X) Transformant

R. oryzae Pyr-17(pLdhA71X) transformant and wild-type R. oryzae NRRL 395 spores obtained from RZ-gly/CAA plates were inoculated equally into five 125 ml flasks containing 50 mls RZ supplemented with 10% (w/v) glucose and 5 mg calcium carbonate/ml. Cultures were incubated for 24 hr at 30° C. and with shaking at 200 rpm. Additional calcium carbonate, 1.25 g/flask, was added and incubation was allowed to continue as before until the glucose was depleted.

Concentrations of glucose, lactic acid, and glycerol were measured by HPLC using Aminex 87-H (Biorad) with R.I. detection. Fumaric acid was measured by same separative methods, but used U.V. absorbance at 210 nm for detection. Ethanol concentrations were determined using gas chromatography.

Efficiency of lactic acid production was significantly higher, based on Student T-test, in the recombinant strain compared to the control. The fermentation for *R. oryzae* Pyr-17(pLdhA71X) was complete 48 hrs after inoculation and the average accumulated lactate levels at this time were 49% higher than the control. The controls continued to ferment the remaining glucose, but total lactic acid levels at 72 hrs were still 76% that achieved for the recombinant strain. The results are reported in Table II, below.

The increase in lactic acid levels were associated with significantly decreased levels in both ethanol and fumaric acid. At 48 hrs, the accumulated levels of ethanol were 74% of the control and accumulated levels of fumaric acid were 48% of the control. The difference in fumaric acid levels were even more profound at 72 hrs with the recombinant strain having only 29% of the average concentration for the control. Glycerol concentrations were not significantly different than the controls at 48 hrs, although they were much less at 72 hrs.

EXAMPLE 5

Expression of ldhA in *E. coli*

*R. oryzae* ldha can be expressed in other hosts, such that high levels of lactic acid production can be achieved. Expression in *E. coli* and *S. cerevisiae* (Example 6) substantiates that other bacteria, yeast, and fungal organisms are potential hosts for successful expression.

Figure 2:
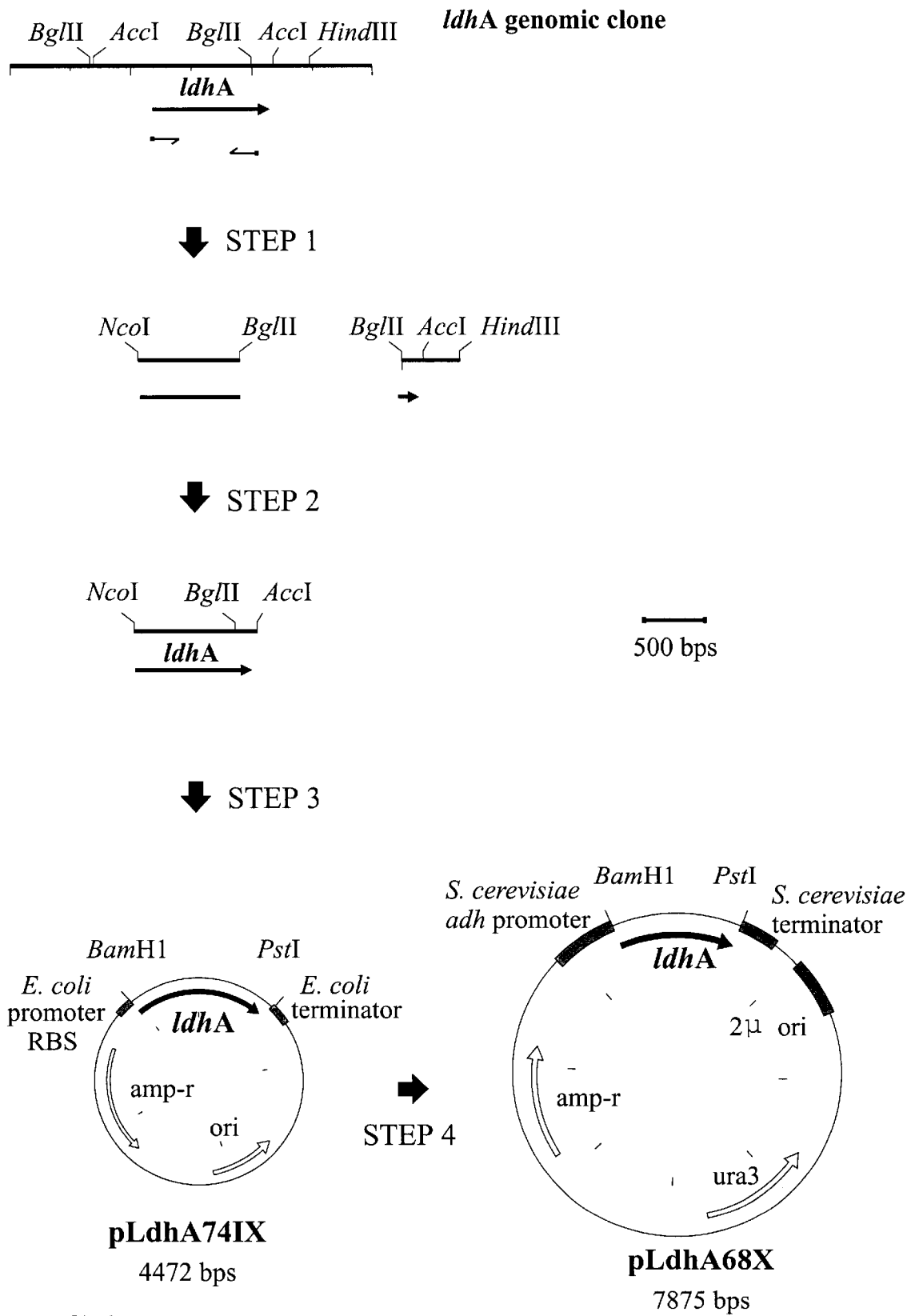
FIG. 2 illustrates the scheme for constructing the pLdhA74IX and the pLdhA68X plasmids used for expressing the *R. oryzae* ldhA gene in *E. coli* and *S. cerevisiae*, respectively.

The *R. oryzae* ldhA gene was modified to be expressed in the bacterial expression vector pQE-30 (Qiagen, Valencia, Calif.). PCR amplification of the ldhA gene with the primers 5'-CC<u>ATGG</u>tattacactcaaaggtcgccatcg-3' (SEQ ID NO 7) and 5'-cgcttcttcttcttccgtcagt-3' (SEQ ID NO 8) was used to introduce an NcoI site at the start codon (FIG. 2, STEP 1). The restriction site NcoI is shown above in SEQ ID NO 7 as capital letters and ATG start codon is underlined. This partial 860 bp ldhA fragment was digested with NcoI and BglII and then ligated to the remaining half of the ldhA represented as a 487 bp BglII/HindIII fragment. Approximately, 306 bp of 3' untranslated region was removed by digestion with AccI (FIG. 2, STEP 2). The resulting 1.0 kb NcoI/AccI was treated with Klenow enzyme and blunt-end ligated into BamH1 linearized pQE-30 treated in the same manner (FIG. 2, STEP 3). After ligation, the BamHI site remained at the 5' end of the gene, immediately upstream of the ATG codon contained in the primer SEQ ID NO 7. The resulting plasmid, pLdhA74IX, contains the ldhA gene operably fused to the *E. coli* T5 promoter and two lac operator sequences. Additionally, the vector sequence contains a synthetic ribosome binding site, RBS, and a transcriptional terminator from phage lambda.

Expression in a prokaryotic organism was performed using *E. coli* DC1368 (thr-1 leu-6 thi-6 lacY tonA22 rpsL ldhA::kan pfl::Cam), kindly provided by D. P. Clark (Southern Illinois University, Carbondale, Ill.). This strain lacks a functional LdhA and pyruvate-formate lyase (Pfl) and is unable to grow anaerobically due to an inability to regenerate $NAD^+$ fermentatively. This strain was transformed with the bacterial ldhA expression plasmid by electroporative methods and is henceforth referred to as *E. coli* DC1368 (pLdhA74IX).

Introduction of the plasmid pLdhA74IX into *E. coli* DC1368 not only restored the ability to grow anaerobically, but resulted in high levels of lactic production. Fermentation studies were performed by growing the untransformed *E. coli* DC1368 control and the transformed strain *E. coli* DC1368 (pLdhA74IX) overnight at 37° C. in YP medium (0.5% yeast extract, 1% peptone) supplemented with 2% (w/v) glucose and appropriate antibiotics to maintain plasmids and/or strain mutations. This culture was then used to seed, with 3% v/v inoculum, fresh YP medium containing 4% (w/v) glucose, antifoam, and 0.5 mM isopropyl-beta-D-thiogalactopyranoside to induce ldhA gene expression from the bacterial promoter. Sterile air or nitrogen was bubbled into the culture medium at 0.5 vvm to test both aerobic growth and anaerobic growth. Sodium hydroxide was added during production of lactic acid to maintain the pH at 6.5.

The recombinant *E. coli* DC1368 (pLdhA74IX) strain produced lactic acid regardless of the aeration, while the control strain produced none. Production of lactic acid was slightly higher under anaerobic conditions presumably because of the absence of acetate production. Conversion of glucose to lactic acid was high with almost 100% yield from the sugars consumed. No growth occurred for the control strain with anaerobic conditions. The results are reported in Table III, below.

EXAMPLE 6

Expression of ldhA in *Saccharomyces cerevisiae*

For expression in *S. cerevisiae*, the ldhA gene was removed from pLdhA74IX on a 1.0 kb BamH1/PstI fragment and ligated to the yeast vector pVT102 [Vernot et al. Gene 52:225–233 (1987)] previously digested with the same enzymes (FIG. 2, STEP 4). The plasmid pVT102 is a 2 micron replicating yeast plasmid that allows expression of cloned genes from the *S. cerevisiae* adh1 promoter. The resulting plasmid, pLdhA68X, was transformed into the haploid yeast *S. cerevisiae* Day 4 (ura3, trp1, leu2, his4, ser1) and diploid *S. cerevisiae* InvScI (Mat-alpha, his3, leu2, trp1, ura3) using uracil auxotrophy as selection. Transformation was conducted using lithium acetate/polyethylene glycol methods. Plasmid pVT102 was transformed into the same strains to serve as controls.

Fermentations were performed as with the above *E. coli*, except growth was at 30° C., initial glucose concentration was 10% (w/v), and pH was maintained at 5.5. No detectable lactic acid was produced by the vector transformed control strains, since *S. cerevisiae* lacks the ability to produce significant lactic acid. Strains, *S. cerevisiae* InvSc1 (pLdhA68X) and *S. cerevisiae* Day 4 (pLdhA68X), containing the recombinant ldhA were able to convert as much as 33% of the total available sugars to lactate in less than 30 hrs. Production rates were significantly higher under anaerobic condition and slightly better for the diploid strain. The results are reported in Table IV, below. The yeast strains employed in this study are able to produce ethanol fermentatively by the enzymes pyruvate decarboxylase and alcohol dehydrogenase. Therefore, the recombinant lactate dehydrogenase must compete for available pyruvate with this highly effective pathway. It is expected that alterations affecting this ethanol production route will further increase the efficiency of lactic acid production by recombinant yeast.

EXAMPLE 7

Forced Integration of DNA into R. oryzae

Unlike most fungi that integrate transforming DNA by homologous recombination, Zygomycetes fungi primarily replicate transformed DNA by unknown methods of autonomous replication. The construction strategy applied as described herein forces the recombinant plasmids to integrate in multiple copy numbers. Such techniques can be extremely useful in applications that require additional gene copies for increasing specific enzymatic activities.

The R. oryzae ldhA has been shown to have extremely strong promoter activity in conditions conducive for lactic acid production. Approximately 424 bp of DNA upstream of the ATG start codon and 313 bp of coding region for the ldha gene were ligated to the 2.25 kb pyrG containing fragment described in Example 1. The combined 3.1 kb ldhA-pyrG was inserted into pBluescriptII KS(−) for selection in E. coli and the resulting plasmid was called pLdhA60X.

Figure 3A:
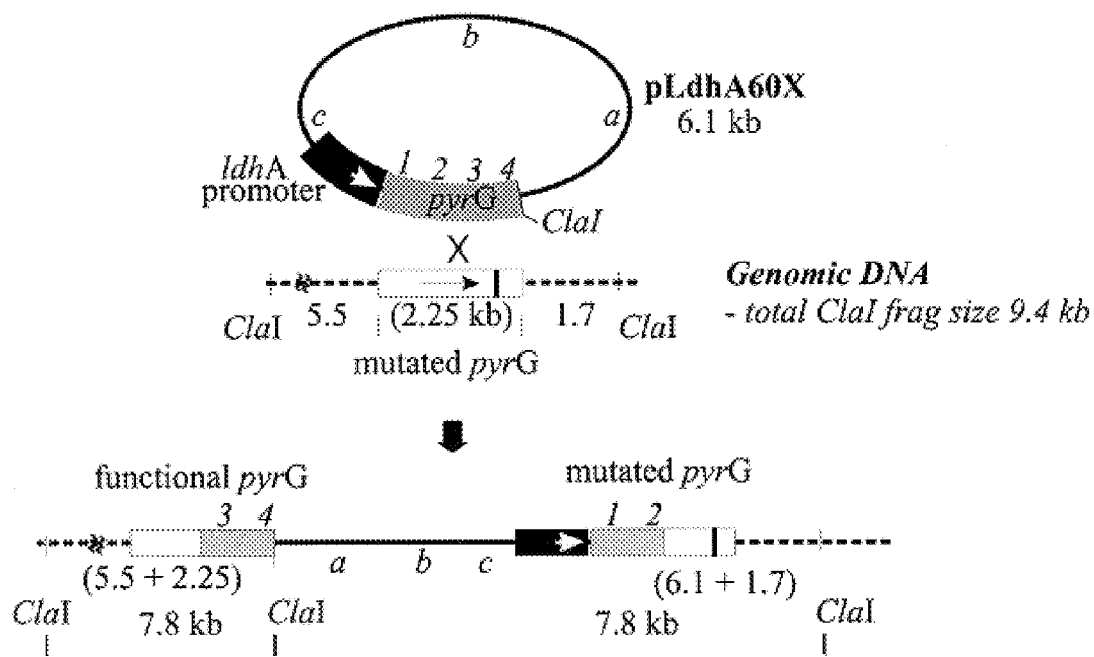
FIG. 3A illustrates a strategy for forced integration of a vector into the genome of Zygomycetes fungi. Functional transcription of the pyrG is prevented by the ldhA promoter activity and is overcome only by single cross-over integration into the genomic pyrG.

The presence of the ldhA promoter region and truncated ldha coding region placed upstream of the pyrG gene serves to interfere with functional expression of the pyrG when conditions are such that ldhA is actively transcribed. Without expression of pyrG, transformants are unable to grow as a result of the auxotrophic selection. However, single crossover integration of the circular plasmid at the genomic pyrG can overcome this inhibition. This is accomplished by creating two copies of the pyrG gene, one of which is now functional and no longer affected by the ldhA promoter (FIG. 3A).

Figure 3B:
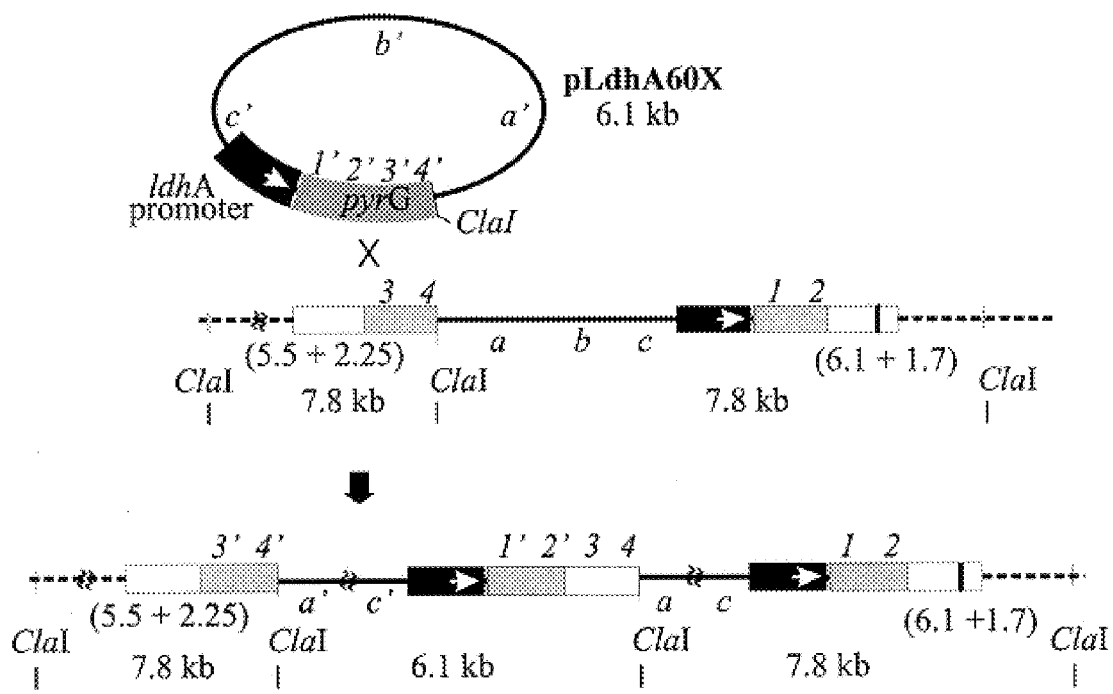
FIG. 3B further illustrates how the integrating plasmid vector will continue to insert multiple copies of the plasmid in tandem formation into the genome.

Additional, copies of the plasmid may continue to integrate in the same manner, thereby increasing copy number of the recombinant construct (FIG. 3B). DNA of interest can be added to the plasmid pLdhA60X at any of numerous unique restriction sites.

As a demonstration of the effectiveness of this system, circular pLdhA60X was transformed into R. oryzae Pyr-17 with selection conditions on both RZ-gluc for induction of the ldhA gene and RZ-gly/caa for non-inducing conditions. Transformation was conducted as described in Example 1. Southern analyses showed that 100% of the ten transformants obtained from the RZ-gluc had between 2–4 copies of pLdhA60X integrated at the pyrG locus. Only one of the ten transformants maintained on RZ-gly/caa had any evidence for integration. It is not surprising that integration occurred in at least one of these transformants, since ldhA is known to be expressed in low levels even in the absence of fermentable sugars.

TABLE I

Reductive lactate dehydrogenase activity by R. oryzae

| strain | units / mg protein[a] | standard deviation | percent control |
|---|---|---|---|
| Pyr-17 (pLdhA71X) | 1.146 | (0.220) | 162% |
| NRRL 395 control | 0.707 | (0.156) | 100% |

[a]average based on triplicates; one unit of enzyme activity is required to reduce 1 micromole NADH / min

TABLE II

Analysis of fermentation products by R. oryzae[a]

| Strain | Time (hrs)[b] | % glucose (w/v) | lactic acid (M) | % ethanol (w/v) | fumaric acid (mM) | glycerol (mM) |
|---|---|---|---|---|---|---|
| NRRL 395 control | 48 hrs | 1.068 (0.275) | 0.447 (0.038) | 1.390 (0.113) | 6.2 (0.8) | 28.6 (1.1) |
| | 72 hrs | 0.118 (0.263) | 0.516 (0.038) | 1.299 (0.140) | 11.0 (1.3) | 32.2 (1.8) |
| Pyr-17 (pLdhA71X) | 48 hrs | 0.224 (0.136) | 0.664 (0.010) | 1.028 (0.043) | 3.0 (0.3) | 30.6 (2.2) |
| | 72 hrs | 0.000 (0.000) | 0.674 (0.008) | 0.927 (0.064) | 3.2 (0.4) | 24.6 (2.6) |

[a]Average based on five separate replicates. Standard deviation shown in parentheses.
[b]Time from inoculation

TABLE III

Analysis of E. coli fermentation at 52 hrs after inoculation

| | Strain | % glucose (w/v) | lactic acid (M) | acetate (M) |
|---|---|---|---|---|
| Anaerobic | DC1368 control | 3.76 | 0.000 | 0.000 |
| | DC1368 (pLdhA74IX) | 0.78 | 0.329 | 0.000 |
| Aerobic | DC1368 control | 2.82 | 0.000 | 0.000 |
| | DC1368 (pLdhA74IX) | 0.13 | 0.322 | 0.024 |

TABLE IV

Analysis of S. cerevisiae fermentation at 30 hrs after inoculation

| | Strain | % glucose (w/v) | lactic acid (M) | % ethanol (w/v) |
|---|---|---|---|---|
| Aerobic | InvScI (pyT102) | 1.29 | 0.000 | 1.67 |
| | InvScI (pLdhA68X) | 0.00 | 0.323 | 1.30 |
| | Day4(pVT102) | 0.00 | 0.000 | 2.00 |
| | Day4(pLdhA68X) | 0.00 | 0.232 | 1.40 |
| Anaerobic | InvSaI (pVT102) | 0.502 | 0.000 | 2.88 |
| | InvScI (pLdhA68X) | 0.000 | 0.370 | 2.22 |
| | Day4(pVT102) | 0.169 | 0.000 | 3.21 |
| | Day4 (pLdhA68X) | 0.000 | 0.314 | 2.57 |

I claim:

1. An isolated nucleic acid fragment of fungal origin comprising a lactate dehydrogenase gene encoding for lactate dehydrogenase having an amino acid sequence having at least 95% sequence identity to SEQ ID NO: 2 and capable of reducing pyruvate to lactate.

2. The fragment of claim 1, wherein said fungal origin is *Rhizopus oryzae*.

3. The fragment of claim 2, wherein said gene is ldhA encoding SEQ ID NO: 2.

4. The fragment of claim 3 having a length of about 6.1 kb or less.

5. The fragment of claim 3 consisting essentially of the ldhA gene encoding SEQ ID NO: 2.

6. An expression cassette comprising a lactate dehydrogenase coding sequence of fungal origin and a promoter operably linked to the coding sequence, wherein said coding sequence encodes an amino acid sequence having at least 95% sequence identity to SEQ ID NO: 2 and capable of reducing pyruvate to lactate.

7. The expression cassette of claim 6, wherein said fungal origin is *Rhizopus oryzae*.

8. The expression cassette of claim 7, wherein said gene is ldhA encoding SEQ ID NO: 2.

9. The expression cassette of claim 8, and further comprising a terminator sequence operably linked to the coding sequence.

10. A host plasmid having inserted therein the fragment of claim 1.

11. A host plasmid having inserted therein the fragment of claim 3.

12. The host plasmid of claim 11, wherein said plasmid is pLdhA71X.

13. A host plasmid having inserted therein the fragment of claim 5.

14. The host plasmid of claim 13, wherein said plasmid is pLdhA74IX or pLdhA68X.

15. A host plasmid having inserted therein the expression cassette of claim 6.

16. A host plasmid having inserted therein the expression cassette of claim 9.

17. The host plasmid of claim 11, wherein said plasmid replicates autonomously or integrates into the genome of a microorganism selected from the group consisting of a bacterium or a fungus.

18. The host plasmid of claim 11, wherein said plasmid replicates autonomously or integrates into the genome of a microorganism selected from the group consisting of *Rhizopus oryzae*, *Escherichia coli*, and *Saccharomyces cerevisiae*.

19. A microrganism transformed with a construct that expresses a fungal lactate dehydrogenase having at least 95% sequence identity to SEQ ID NO: 2 and capable of reducing pyruvate to lactate.

20. The microorganism of claim 19, wherein said microorganism is a bacterium or a fungus.

21. The microorganism of claim 19, wherein said microorganism is selected from the group consisting of *Rhizopus oryzae, Escherichia coli* and *Saccharomyces cerevisiae*.

22. The microorganism of claim 19, wherein said construct is genomically integrated.

23. The microorganism of claim 19, wherein said construct comprises a *Rhizopus oryzae* ldhA gene encoding SEQ ID NO: 2.

24. The microorganism of claim 19, wherein said construct is a plasmid.

25. The microorganism of claim 19, wherein said microorganism is selected from the group consisting of *Rhizopus oryzae* NRRL 30272, *Escherichia coli* NRRL B-30273, and *Saccharomyces cerevisiae* NRRL Y-30271.

26. A method of producing lactic acid comprising culturing the microorganism of claim 19 in a fermentable medium.

27. The method of claim 26, wherein said microorganism is a bacterium or a fungus.

28. The method of claim 26, wherein said microorganism is selected from the group consisting of *Rhizopus oryzae, Escherichia coli*, and *Saccharomyces cerevisiae*.

29. The method of claim 26, wherein said construct comprises a *Rhizopus oryzae* ldhA gene encoding SEQ ID NO: 2.

* * * * *

SEQUENCE LISTING

<160> NUMBER OF SEQ ID NOS: 8

<210> SEQ ID NO 1
<211> LENGTH: 1116
<212> TYPE: DNA
<213> ORGANISM: Rhizopus oryzae
<220> FEATURE:
<221> NAME/KEY: CDS
<222> LOCATION: (32)..(994)

<400> SEQUENCE: 1

```
ttactttatt tttctttaca atataattct c atg gta tta cac tca aag gtc         52
                                  Met Val Leu His Ser Lys Val
                                    1               5 gcc atc gtt gga gct ggt gca gta gga gcc tcc act gct tat gca ctt       100
Ala Ile Val Gly Ala Gly Ala Val Gly Ala Ser Thr Ala Tyr Ala Leu
         10                  15                  20 atg ttt aaa aac att tgt aca gaa atc att att gtt gat gtt aat cct       148
Met Phe Lys Asn Ile Cys Thr Glu Ile Ile Ile Val Asp Val Asn Pro
 25                  30                  35 gac atc gtt caa gct caa gtc ctt gac ctt gca gat gct gcc agt ata       196
Asp Ile Val Gln Ala Gln Val Leu Asp Leu Ala Asp Ala Ala Ser Ile
 40                  45                  50                  55 agt cac acg ccc atc cga gca ggt agc gca gag gag gca ggg cag gca       244
Ser His Thr Pro Ile Arg Ala Gly Ser Ala Glu Glu Ala Gly Gln Ala
                 60                  65                  70 gat att gtt gtc atc acg gcc ggt gcg aaa caa agg gaa ggt gag cct       292
Asp Ile Val Val Ile Thr Ala Gly Ala Lys Gln Arg Glu Gly Glu Pro
             75                  80                  85 cgg aca aag ctc att gaa cga aac ttc aga gtg ttg caa agt atc att       340
Arg Thr Lys Leu Ile Glu Arg Asn Phe Arg Val Leu Gln Ser Ile Ile
         90                  95                 100 ggt ggc atg caa ccc att cga cca gac gca gtc atc ttg gtg gta gca       388
Gly Gly Met Gln Pro Ile Arg Pro Asp Ala Val Ile Leu Val Val Ala
     105                 110                 115 aat cca gtc gat atc ttg aca cac att gca aag acc ctc tct gga ctg       436
Asn Pro Val Asp Ile Leu Thr His Ile Ala Lys Thr Leu Ser Gly Leu
120                 125                 130                 135 cct cca aac cag gtc att ggc tcc ggt acc tac ctt gac acg acc cgt       484
Pro Pro Asn Gln Val Ile Gly Ser Gly Thr Tyr Leu Asp Thr Thr Arg
                140                 145                 150 ctt cgc gtc cat ctt ggc gat gtc ttt gat gtc aat cct caa tcg gtc       532
Leu Arg Val His Leu Gly Asp Val Phe Asp Val Asn Pro Gln Ser Val
            155                 160                 165 cat gct ttt gtc ttg ggt gaa cat ggg gat tcc cag atg atc gct tgg       580
His Ala Phe Val Leu Gly Glu His Gly Asp Ser Gln Met Ile Ala Trp
        170                 175                 180 gag gct gct tcg att ggt ggc cag ccg ttg aca agt ttc ccg gaa ttc       628
Glu Ala Ala Ser Ile Gly Gly Gln Pro Leu Thr Ser Phe Pro Glu Phe
    185                 190                 195 gca aag ctg gat aaa aca gca att tca aaa gcg ata tca ggt aaa gcg       676
Ala Lys Leu Asp Lys Thr Ala Ile Ser Lys Ala Ile Ser Gly Lys Ala
200                 205                 210                 215 atg gag atc att cgt ttg aaa gga gcc acg ttt tat gga att ggt gcc       724
Met Glu Ile Ile Arg Leu Lys Gly Ala Thr Phe Tyr Gly Ile Gly Ala
                220                 225                 230 tgt gca gcg gat tta gtg cac act atc atg ttg aat agg aaa tca gta       772
Cys Ala Ala Asp Leu Val His Thr Ile Met Leu Asn Arg Lys Ser Val
            235                 240                 245
```

```
cat cca gtt tct gtt tat gtt gaa aag tat gga gcc act ttt tct atg       820
His Pro Val Ser Val Tyr Val Glu Lys Tyr Gly Ala Thr Phe Ser Met
        250                 255                 260 cct gct aaa ctt gga tgg aga ggt gtt gaa cag atc tat gaa gta cca       868
Pro Ala Lys Leu Gly Trp Arg Gly Val Glu Gln Ile Tyr Glu Val Pro
265                 270                 275 ctg acg gaa gaa gaa gaa gcg ttg ctt gta aaa tct gta gag gca ttg       916
Leu Thr Glu Glu Glu Glu Ala Leu Leu Val Lys Ser Val Glu Ala Leu
280                 285                 290                 295 aaa tca gtt gaa tat tca tct aca aaa gtt cca gaa aaa aag gtt cat       964
Lys Ser Val Glu Tyr Ser Ser Thr Lys Val Pro Glu Lys Lys Val His
            300                 305                 310 gct act tcc ttt tct aaa agt agc tgt tga taatttacaa ataataaatc        1014
Ala Thr Ser Phe Ser Lys Ser Ser Cys
            315                 320 atgttttgca ctgctagtgt atacataaag aaaaagttaa tagtcagttg ttatactcgg    1074
tgtagctaat tttttgaatg atacttttaa ttacaatatt at                       1116
```

<210> SEQ ID NO 2
<211> LENGTH: 320
<212> TYPE: PRT
<213> ORGANISM: Rhizopus oryzae

<400> SEQUENCE: 2

```
Met Val Leu His Ser Lys Val Ala Ile Val Gly Ala Gly Ala Val Gly
 1               5                  10                  15

Ala Ser Thr Ala Tyr Ala Leu Met Phe Lys Asn Ile Cys Thr Glu Ile
                20                  25                  30

Ile Ile Val Asp Val Asn Pro Asp Ile Val Gln Ala Gln Val Leu Asp
            35                  40                  45

Leu Ala Asp Ala Ala Ser Ile Ser His Thr Pro Ile Arg Ala Gly Ser
    50                  55                  60

Ala Glu Glu Ala Gly Gln Ala Asp Ile Val Ile Thr Ala Gly Ala
 65                 70                  75                  80

Lys Gln Arg Glu Gly Glu Pro Arg Thr Lys Leu Ile Glu Arg Asn Phe
                85                  90                  95

Arg Val Leu Gln Ser Ile Ile Gly Gly Met Gln Pro Ile Arg Pro Asp
            100                 105                 110

Ala Val Ile Leu Val Val Ala Asn Pro Val Asp Ile Leu Thr His Ile
            115                 120                 125

Ala Lys Thr Leu Ser Gly Leu Pro Pro Asn Gln Val Ile Gly Ser Gly
    130                 135                 140

Thr Tyr Leu Asp Thr Thr Arg Leu Arg Val His Leu Gly Asp Val Phe
145                 150                 155                 160

Asp Val Asn Pro Gln Ser Val His Ala Phe Val Leu Gly Glu His Gly
                165                 170                 175

Asp Ser Gln Met Ile Ala Trp Glu Ala Ala Ser Ile Gly Gly Gln Pro
            180                 185                 190

Leu Thr Ser Phe Pro Glu Phe Ala Lys Leu Asp Lys Thr Ala Ile Ser
        195                 200                 205

Lys Ala Ile Ser Gly Lys Ala Met Glu Ile Ile Arg Leu Lys Gly Ala
    210                 215                 220

Thr Phe Tyr Gly Ile Gly Ala Cys Ala Ala Asp Leu Val His Thr Ile
225                 230                 235                 240

Met Leu Asn Arg Lys Ser Val His Pro Val Ser Val Tyr Val Glu Lys
                245                 250                 255
```

-continued

Tyr Gly Ala Thr Phe Ser Met Pro Ala Lys Leu Gly Trp Arg Gly Val
            260                 265                 270

Glu Gln Ile Tyr Glu Val Pro Leu Thr Glu Glu Glu Ala Leu Leu
        275                 280                 285

Val Lys Ser Val Glu Ala Leu Lys Ser Val Glu Tyr Ser Ser Thr Lys
        290                 295                 300

Val Pro Glu Lys Lys Val His Ala Thr Ser Phe Ser Lys Ser Ser Cys
305                 310                 315                 320

```
<210> SEQ ID NO 3
<211> LENGTH: 6072
<212> TYPE: DNA
<213> ORGANISM: Rhizopus oryzae
<220> FEATURE:
<221> NAME/KEY: misc_feature
<222> LOCATION: (3100)..(4062)

<400> SEQUENCE: 3
```

| | | | | | |
|---|---|---|---|---|---|
| gatcattaaa | cctgttgcac | acatatttga | aaatgcattc | tggattggta | agttatagtt | 60 |
| gagctgtact | actttatgta | ctcaactaga | gttactttt | taggtgtggc | tgtggtgacc | 120 |
| atattggata | acaccgtcgg | tggttttctt | acactcagtt | ttcaaagaat | tattggtact | 180 |
| gtggttggtg | gtgtgttgag | tatcattgtc | atgaccgtcg | ttcgtgctat | ctttcaaccc | 240 |
| cagtgggatg | caagagctgc | tgtcttgctc | tgtttcttta | tgtttgctca | agttttatt | 300 |
| atcgcaagac | tcaaacaact | tcccaactac | tcttatgcag | gcggcattgt | aaatatattc | 360 |
| tctcagtggt | ttacatttag | tttattgact | tggtttattt | tagggtttgt | taacgaccgg | 420 |
| ttattatctt | gttatctggt | tataacgata | taattcatgg | tcgattatcc | agagatcaga | 480 |
| acttggtgca | tggagaacat | gcaacttggt | gatcggtata | gtgcttgcaa | tgtaagtcaa | 540 |
| tctgagcctt | aaaaaatat | gtcgggtgtc | ttggtattcc | aatcatttaa | tttcttatct | 600 |
| taggatggtt | tcattttgtg | tctttcctgt | tacatccact | ggcataatga | gagcaaacct | 660 |
| cggaaaatca | atggagaaat | ccgctaattt | atatcaaaga | ctggcagaat | tttatcttga | 720 |
| tttcaaacaa | ggagaatcag | atcattcttt | ggcttctatg | ctagaacgta | aggcaccgat | 780 |
| agatgaagaa | caagaaccac | cttctataaa | agaaacactt | caacgtatct | ttcaaatac | 840 |
| ccaaacggat | ccacaagtag | aacagaacca | ggtctggaca | aatgacgaaa | tcacaagtat | 900 |
| cagtaacgaa | gctatctcca | ttctctttca | gcttcagaca | gaatctacac | gcttaagaaa | 960 |
| cgtatccaat | gaatacaact | ttcggctctt | tttttatttt | ctcgagggag | gcaaggatca | 1020 |
| ctgcaagcga | tacatgcgcc | gtgcgaaaag | atacaatgaa | gcgatcgatg | ccctcaaacg | 1080 |
| gaccgtttgg | ccacttgcct | cctttcgctt | gctgtttcct | ctcattcact | ctgaacaaaa | 1140 |
| ggcgaggatg | atacccacaa | gagaaacgct | tgaatgcttt | accgatagtc | tcacagtgat | 1200 |
| gcgaaaactc | ggatcgatcc | tgaaggatcg | tcaacgtccg | ctgagtgatt | ttaaagaaga | 1260 |
| ttggttggag | attcatcgga | tggtggctgc | tgggaatgca | catgctcagc | gcgagctcaa | 1320 |
| agagacggtt | caaatcggga | tgaatcatca | aaacatggat | ggttacaagt | tgctttctta | 1380 |
| ttatggattc | ctcgtcagat | tttcggcgat | tgggacgga | ttgaaaacag | tagtagacct | 1440 |
| gctgagcccg | ttgaacggtg | ctttgagccg | tcctggttct | gttcaaagtg | aatccacttg | 1500 |
| tttaccaaat | agggaagtga | ttcatgtacc | cgaataatat | atattttctt | tataataaat | 1560 |
| ttcttattt | gcttatctac | caaatcaagt | cgcattttgt | ttgagatatg | ttaccgtagt | 1620 |
| actattatcc | attagattat | ttctgttta | atcaatgttt | ttaattttca | tggcgtgtgc | 1680 |

```
gtgtgtgaca cgaagcacag aaaaagtaaa aaaatactaa atctaaaacc aagtcaaagc    1740
gttcaaagga gataacaaag cgtgatttaa tactttatg gcgtagatca tttcttttt     1800 ttatgtgagc aaactgactg aaactacagt attccctcgt gaattttaag tgtgacttta   1860
gtatcttttg atgatcatac tttgtttgtt aagctctggg tcttattctc gtctttaaa    1920 acaaggaagg tggttcatgc aaatttaaat tcagttgtat tccatttact ttctcatccc   1980 ccccccctt ttttgtact tgaacccgaa attttgtttg agttatcttt gttgtatgaa     2040
atagaattaa attaaatttg atcactatct ggtttcatat caaaacaaaa ctacttatca   2100
ttcacgcggt aaaactcaaa taaaaaataa tacaagtttt atttatatta aaagacttga   2160
atgagtacgt agtgtcctca ctctaatccc cccccggagt cagatcaaaa gggagcataa   2220
gggaattttt taaaaaaaaa aaagaataag aaaagatgtg tcaggacgtc aaattcaaag   2280
aagatcagat aaacggcggg tcaacagaga tagaatgaaa cgaacgtgac ttgtagggta   2340
agtagtaagt ttggagggaa aaacaaaact ttgatagtaa atgatatttt aaaacaaatt   2400
gattagttga attaatttat tttcttaaca atctagataa ttttcttta ctgtacacag    2460 ttgatcttgc ttgtgtttct ttttgattct cagtttatag aatcgaagca gtcaatgtac   2520
tttatctttt catatctaaa ttaaagtaat cgtatgttcc ttcttaaatg ccgcatgaga   2580
ttacccaaga tctccatgct atacaattta aaacgatgtc tactttagtc tcttcttttt   2640
acatttgatc atgtcaattt ttaaagatcg cggtggatgc tttttcgata agatatcag    2700 tgtatttgaa tggaactacg ttataaggct ctggggccct gtaatagaaa ccatgtttga   2760
taatacaggt ttaaggctga ggctcagatg gtagcattat gtttcacttt attttattc    2820 tatctggaca tattgttaaa ggtgatacca tcttaatttg cctttattgt tattattatc   2880
accaattagt ctattttaa tggaatgtat tgttttggat tacttatgaa ccatggcatc    2940
tatgccagca attcatgtac gactgtactc ttatactgtt ttttttcctt ttaagcggtc   3000
catgtctctg tgtgtataac atgagcttgc aagtccgaat atgcaaaaag tatataaatc   3060
aatgctggtt actttatttt tcttttacaat ataattctca tggtattaca ctcaaaggtc  3120
gccatcgttg gagctggtgc agtaggagcc tccactgctt atgcacttat gtttaaaaac   3180
atttgtacag aaatcattat tgttgatgtt aatcctgaca tcgttcaagc tcaagtcctt   3240
gaccttgcag atgctgccag tataagtcac acgcccatcc gagcaggtag cgcagaggag   3300
gcagggcagg cagatattgt tgtcatcacg gccggtgcga aacaaaggga aggtgagcct   3360
cggacaaagc tcattgaacg aaacttcaga gtgttgcaaa gtatcattgg tggcatgcaa   3420
cccattcgac cagacgcagt catcttggtg gtagcaaatc cagtcgatat cttgacacac   3480
attgcaaaga ccctctctgg actgcctcca aaccaggtca ttggctccgg tacctacctt   3540
gacacgaccc gtcttcgcgt ccatcttggc gatgtctttg atgtcaatcc tcaatcggtc   3600
catgcttttg tcttgggtga acatggggat tcccagatga tcgcttggga ggctgcttcg   3660
attggtggcc agccgttgac aagtttcccg gaattcgcaa agctggataa acagcaatt    3720 tcaaaagcga tatcaggtaa agcgatggag atcattcgtt tgaaaggagc cacgttttat   3780
ggaattggtg cctgtgcagc ggatttagtg cacactatca tgttgaatag gaaatcagta   3840
catccagttt ctgtttatgt tgaaaagtat ggagccactt tttctatgcc tgctaaactt   3900
ggatggagag tgttgaaca gatctatgaa gtaccactga cggaagaaga agaagcgttg    3960
cttgtaaaat ctgtagaggc attgaaatca gttgaatatt catctacaaa agttccagaa   4020
```

-continued

```
aaaaaggttc atgctacttc cttttctaaa agtagctgtt gataatttac aaataataaa    4080
tcatgttttg cactgctagt gtatacataa agaaaagtt aatagtcagt tgttatactc    4140
ggtgtagcta atttttttgaa tgatactttt aattacaata ttatttatat ctttttactc    4200
tgatctttga acttgtatat gaaatagata ttccaacaaa gcaaaaattc catgcataaa    4260
tgcacgaaaa aaaggttatt tataatatgt tttaatttac aatcgaattg taaatcgtac    4320 acaatttat gaacctattt tatgcaatta agaactacaa acagagcagt tttctgtttt    4380
actttcttca aaacaaaact aagcttattg gctttatata agtatagaa aaactagata    4440 aaagagtgtg attggataga aacaatctac tgtaattttg accaatattt caagctggag    4500
ttgttctagc ttatagataa aataaagata caaaagaatt taatcacaag ctatagatat    4560
ggcatacaat tgaaagttaa aatgaccgtg tatgagggt attgttgttg ctgtaagctg    4620
ggaatgcctg taccacagat atacccgtgt acaatcataa gaagggatac agaaattcag    4680
ttgttagctg taaaacctt atactttact cgtaacaatc ttccttgata tctcattcga    4740
caatatgacg cccaaatata aaagagagtt tattatccat gacttaaaag tagaacaata    4800
agttccaata aatcattaat ccatctttcc ctgacctgta cccattcttc actcatcact    4860
aatgtatgcc tttctaaatt aagcaatgca ccggccagat gtctctctga tcttcctgtg    4920
ctcactaatg tgagccacgt ctctcttcct tcaagccaag cctcacagac agcagtccat    4980
agtaaggcca tttctaactg gacaagttgg taggctactt gctcagtact gtttggttcc    5040
cttgatagcc atgtttgtcg tttagataac catttgggtg atttatgtcg attgtttatg    5100
tagaattcgt aaaggattat tttgttgttt aatgctttga tactactgag tatagatgtt    5160
tcatatgaag gaggtgcttc atgtgatgtg gatggtatcg aaaatgcagg aggtggactt    5220
tctgatctta ttactactac ttcatcctct gttgttgaat tatcgttatg ttcttcgaca    5280
tattcttctt cctcttcttc gtcatcatca tcgtcttcga tatctgcatc tgcattttgt    5340
atgtctgtta tgattgtttg gctgtgttcc tcttcctcgc cttcagttgt ggttgctgtt    5400
atattactgg tattgtcttg taaccttta aagagcttgc tttgattaac cttaaataaa    5460
agttaaaata tggcaactaa ctcgaactaa ggtcagtagc ttagaaatga ttttataagt    5520
acttcaaaag atgttacttt tagtaccttt tagtatctt tagtaacttt aaagtaactc    5580
caaaatgcaa aagctgacac ctatttcaag ttaattttta actttaactt aaaattaact    5640
ttatttgaaa ctaaaaattt ttagtgttaa ttgatatttt gttataccaat attgtgacat    5700 gttccatatg aaagttgtaa attttaatt tgatatctga ttgaataaat gatgaatatt    5760
ctcagcaatt tatttgtttc caattgcaat ttccggtgat aataatgaag ccaatttctt    5820
cagttgtcta ttcatgtctt tgtttccaag tattttgatt gatgaattat cttcaatgta    5880
tgacttttca atataagcaa atgtttggtc tatttcccct tgttgtttag tgcattgggt    5940
tcttaggaac gcaactgtgt tttggtctaa acttgcttca gcactcttct ttcatacttg    6000
acttgcaatg tgtctaaata atttagaagc agctacacca ctagaatccc tatcctggtt    6060
cctcgagcga tc                                                          6072
```

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:PCR Primer

<400> SEQUENCE: 4

```
attgayattg tkgaagactt yga                                              23

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PCR Primer

<400> SEQUENCE: 5
ccactctcma caatnacttc                                                  20

<210> SEQ ID NO 6
<211> LENGTH: 17
<212> TYPE: DNA
<213> ORGANISM: Artificial Sequence

<400> SEQUENCE: 6
swrtcdccrt gytcacc                                                     17

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:PCR Primer

<400> SEQUENCE: 7
ccatggtatt acactcaaag gtcgccatcg                                       30

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:PCR Primer

<400> SEQUENCE: 8
cgcttcttct tcttccgtca gt                                               22
```